(12) United States Patent
Di Cesare

(10) Patent No.: US 7,909,963 B2
(45) Date of Patent: Mar. 22, 2011

(54) METHOD FOR MEASURING HYDROPHOBIC CONTAMINANTS IN PAPER PULP

(75) Inventor: Nicolas Di Cesare, Drummondville (CA)

(73) Assignee: Cascades Canada Inc., Kingsey Falls, Quebec (CA)

( * ) Notice: Subject to any disclaimer, the term of this patent is extended or adjusted under 35 U.S.C. 154(b) by 350 days.

(21) Appl. No.: 12/096,577

(22) PCT Filed: Jan. 18, 2007

(86) PCT No.: PCT/CA2007/000070
§ 371 (c)(1),
(2), (4) Date: Jun. 6, 2008

(87) PCT Pub. No.: WO2007/082376
PCT Pub. Date: Jul. 26, 2007

(65) Prior Publication Data
US 2008/0308241 A1      Dec. 18, 2008

Related U.S. Application Data

(60) Provisional application No. 60/759,586, filed on Jan. 18, 2006.

(51) Int. Cl.
*D21F 11/00* (2006.01)
(52) U.S. Cl. ........................................ 162/198; 356/338
(58) Field of Classification Search .................. 162/198; 356/338, 343
See application file for complete search history.

(56) References Cited

U.S. PATENT DOCUMENTS

| | | |
|---|---|---|
| 5,486,904 A | 1/1996 | Horn et al. |
| 5,940,177 A | 8/1999 | Esser et al. |

OTHER PUBLICATIONS

Degerth, et al., "Flow Cytometry for Rapid Characterization of Colloidal Particles of Various Types in Process Waters—MPK 05," Laboratory of Forest Products Chemistry, Abo Akademi (Sep. 2001): pp. 1-15.

Lorencak, et al., "Cationic Polymer Additions Overcome Manufacturing Problems Caused by Resins and Mechanical Pulp Extractives," BASF Corporation, Journal of Pulp and Paper Science: vol. 25 No. 1 (Jan. 1999): pp. 1-7.

Whitten, et al., "Use of a Solid-State Fluorometer for Surface Fluorescence Measurements in Pulping and Papermaking Systems," Journal of Pulp and Paper Science, vol. 25 No. 1 (Jan. 1999): pp. 21-24.

*Primary Examiner* — Mark Halpern
(74) *Attorney, Agent, or Firm* — Sutherland Asbill & Brennan LLP

(57) ABSTRACT

A method is provided for measuring hydrophobic contaminants distributed in paper pulp suspension. The method comprises: adding a fluorescent dye (18) to the paper pulp suspension (12) including fibers and hydrophobic contaminants, the dye (18) interacting with the hydrophobic contaminants of the paper pulp suspension (12); submitting the paper pulp suspension (12) including the fibers, the hydrophobic contaminants, and the dye (18) to light characterized by a wavelength exciting the dye (18) to produce light emission signals; and detecting the light emission signals and evaluating the signals to measure the hydrophobic contaminants.

26 Claims, 18 Drawing Sheets

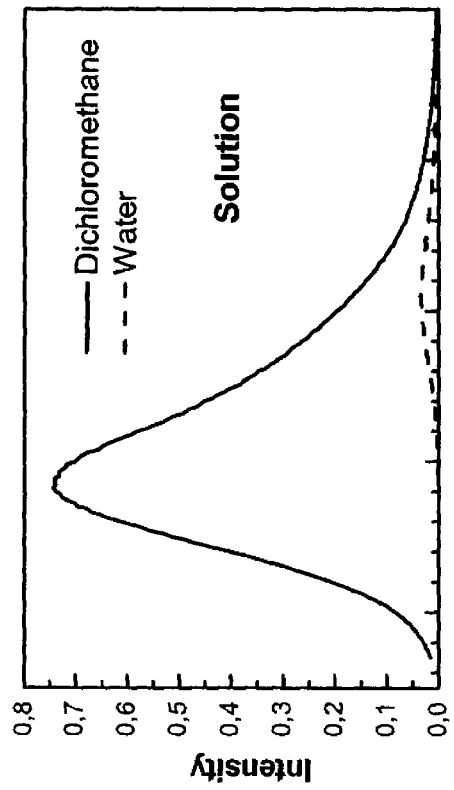
Figure 3a
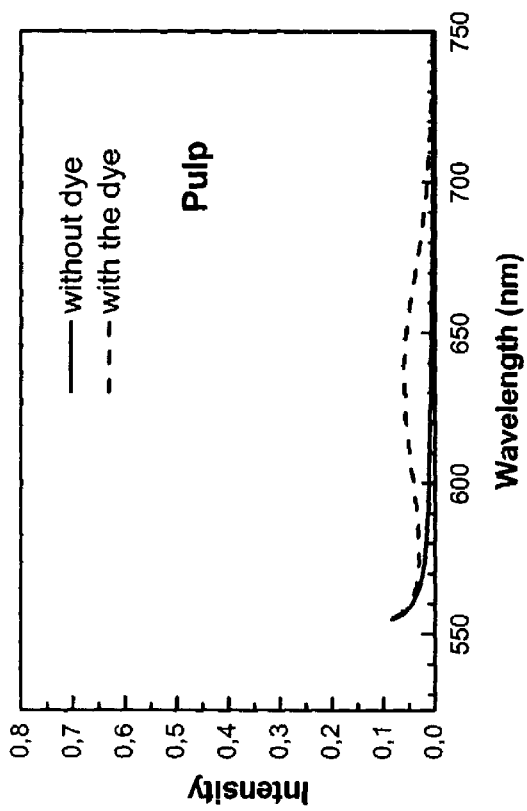
Figure 3b
FIGURE 3

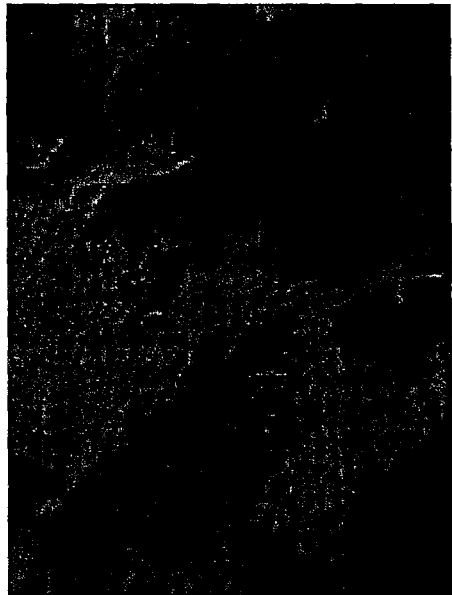
Figure 4b
Figure 4c
Figure 4a
FIGURE 4

METHOD FOR MEASURING HYDROPHOBIC CONTAMINANTS IN PAPER PULP

This application is a 371 of PCT/CA2007/000070 filed 18 Jan. 2007.

BACKGROUND OF THE INVENTION

1) Field of the Invention

The invention relates to a method for monitoring contaminants in paper pulps and, more particularly, it relates to a method and an apparatus for measuring hydrophobic contaminants in paper pulp suspensions.

2) Description of the Prior Art

The presence of contaminants in paper pulp suspension made from recovery fibers is one of the most important problems in paper mills. Therefore, contaminants control and removal is one of the biggest challenges in the use of recovery fibers. Despite the fact that many methods have been developed for the measurement of contaminants, as evidence by: [M. R. Doshi et al., <<Comparison of Macrostickies Measurement Methods >>, Progress in Paper Recycling, 12(3), 34 (2003); M. R. Doshi et al., <<Comparison of Microstickies Measurement Methods, Part I: Sample Preparation and Measurement Methods >>, Progress in Paper Recycling, 12(4), 35 (2003); M. R. Doshi et al., <<Comparison of Microstickies Measurement Methods, Part II: Results and Discussion >>, Progress in Paper Recycling, 12(4), 35 (2003); J. Kortmeyer et al., <<Identification and quantification of process contaminants from paper mills using old corrugated containers >>, 7$^e$ Forum de recherche sur le recyclage, 125 (2004); C. Castro, G. M. Dorris, <<Measuring Microstickies Deposition by Monitoring Pressure Drop Through a Collector >>, Progress in Paper Recycling, 13(3), 23 (2004)], there is still several needs. For instance, all the above methods need specific equipment, extended manipulation and time, thereby preventing their application to large industrial scale. These methods are limited to laboratory level. In addition, the results obtained from these different methods do not always correlate together [M. R. Doshi et al., <<Comparison of Macrostickies Measurement Methods >>, Progress in Paper Recycling, 12(3), 34 (2003); M. R. Doshi et al., <<Comparison of Microstickies Measurement Methods, Part II: Results and Discussion >>, Progress in Paper Recycling, 12(4), 35 (2003)].

U.S. Pat. No. 5,486,904 describes a method for determining the number and the size of resin particles in a pulp suspension. The measurement involves making a pulp suspension; separating resin particles from the pulp suspension by filtration; marking the resin particles with a fluorescent dyestuff and, after singling the resin particles, stimulating light emission; detecting the light signals of the individual resin particles; and evaluating the detection signals to count and determine the size of the resin particles. However, the technique proposed can be difficulty adapted for on-line measurement since the resin particles have to be separated from the pulp suspension.

Similarly, U.S. Pat. No. 5,940,177 describes a method and an apparatus to determine the size distribution of at least two different species in a pulp sample. However, the technique proposed requires separating the contaminant-free particles from the particles including contaminants. Therefore, it is not well suited for on-line measurement.

No fast and easy-to-use instrument for contaminants measurement directly in a paper pulp suspension is available, and only few mills have the time, the equipment and the technical skill to use the laboratory methods described in the literature.

BRIEF SUMMARY OF THE INVENTION

It is therefore an aim of the present invention to address the above mentioned issues.

One aspect of the invention provides a method for measuring directly the contaminants in a paper pulp suspension.

According to a general aspect, there is provided a method for measuring hydrophobic contaminants distributed in a paper pulp suspension. The method comprises: adding a lipophilic fluorescent dye to the paper pulp suspension including fibers and hydrophobic contaminants, the lipophilic fluorescent dye interacting with the hydrophobic contaminants showing fluorescence, whereas the lipophilic fluorescent dye interacting with the fibers showing substantially no fluorescence; submitting the paper pulp suspension including the fibers, the hydrophobic contaminants, and the lipophilic fluorescent dye to light characterized by a wavelength exciting the lipophilic fluorescent dye interacting with the hydrophobic contaminants to produce light emission signals; and detecting the light emission signals and evaluating the signals to measure the hydrophobic contaminants.

According to another general aspect, there is provided a method for monitoring hydrophobic contaminants in a paper pulp suspension containing hydrophilic fibers and hydrophobic contaminants, the method comprising: a) selecting a fluorescent dye having higher fluorescent intensities in hydrophobic environments than in hydrophilic environments, b) mixing the fluorescent dye with the paper pulp suspension to obtain a mixture, and c) monitoring the hydrophobic contaminants in the paper pulp suspension by observing and analysing the fluorescence intensity variations in the mixture.

BRIEF DESCRIPTION OF THE DRAWINGS

FIG. 3a is a graph showing the effect of the solvent polarity on the fluorescence intensity of Nile red;

FIG. 3b is a graph showing the fluorescence of Nile red in a fiber suspension;

FIG. 4a is a photograph of recycled pulp constituents dyed with Nile red;

FIG. 4b is a photograph showing the visibility of only fluorescent constituents upon UV excitation;

FIG. 4c is a photograph showing the visibility of only the fluorescent contaminant upon UV excitation and after blue light removal using a glass color filter;

It will be noted that throughout the appended drawings, like features are identified by like reference numerals.

DETAILED DESCRIPTION OF THE PREFERRED EMBODIMENTS

Figure 1:
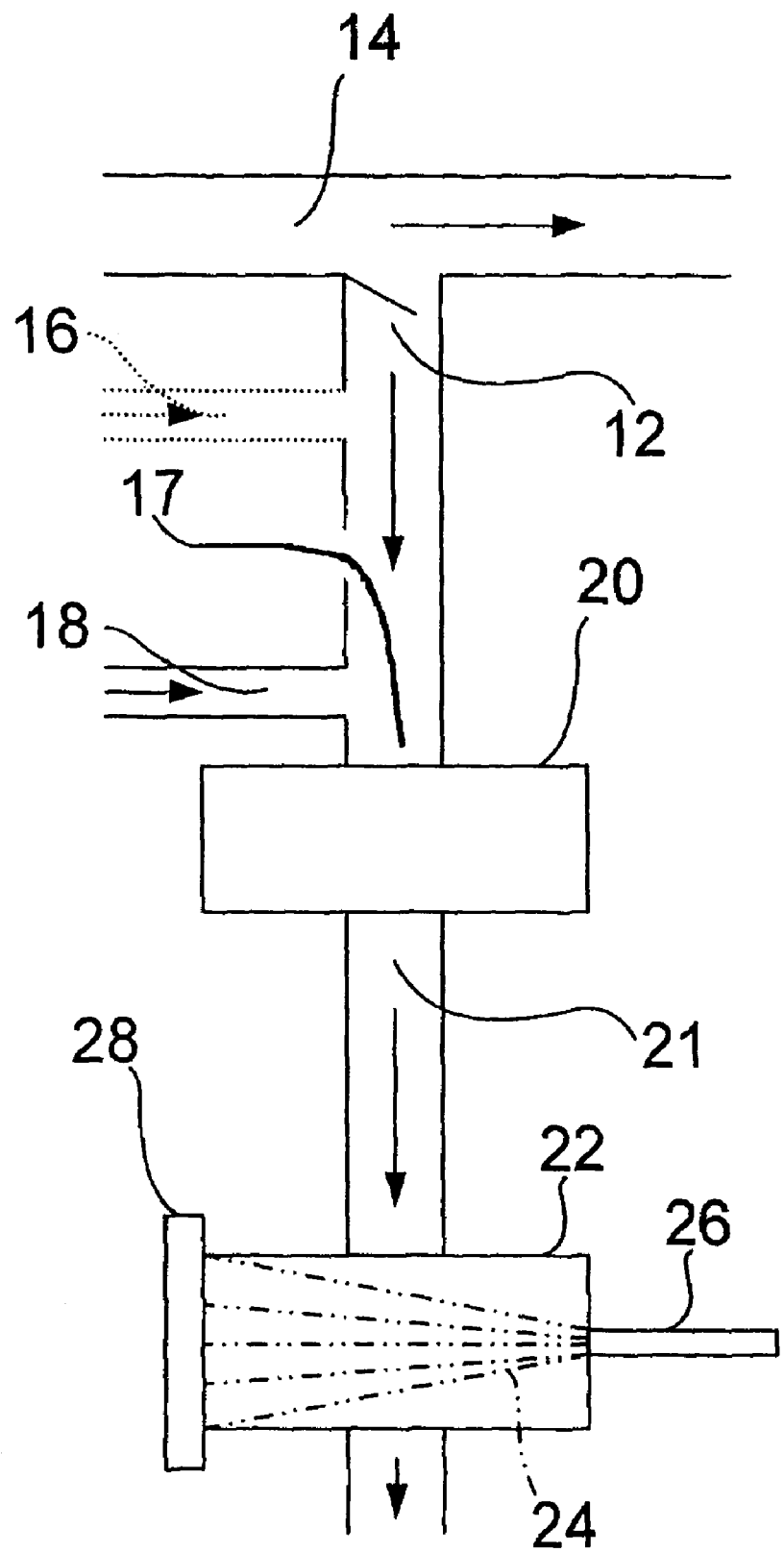
FIG. 1 is a schematic flowsheet of a method for measuring the contaminants in a pulp suspension in accordance with an embodiment of the invention.

Referring now to the drawings and, more particularly, to FIG. 1, there is shown a schematic flowsheet of a method for measuring the contaminants in a pulp suspension.

The principle of the measurement method is based on the hydrophobic properties of the contaminants. Hydrophobic contaminants can include stickies, hot melts, wax, pitch, PVAc, acrylate, SBR, EVA, PE, etc. Most fluorescent dyes (or probes) interact with the hydrophobic contaminants since the fluorescent probes are themselves lipophilic. Once added to the pulp suspension, only dye molecules interacting with the contaminants show fluorescence because of the hydrophobic environment of these contaminants. Dye molecules interacting with other constituents of the pulp suspension, mostly fibers, do not show significant fluorescence.

A pulp sample 12 is taken from a paper pulp flow 14. If necessary, the pulp sample 12 is diluted 16 to a predetermined concentration. A selective fluorescent dye 18 is added in a predetermined quantity to the pulp sample 12 to obtain a secondary pulp sample 17. The mixture pulp suspension and dye 18 is stirred is a stirring device 20 to obtain a stirred mixture 21 during a certain time period. Then, the stirred mixture 21 is sent to a flow cell 22 in which it is submitted to a particular light 24 generated by an excitation beam 26. The hydrophobic contaminants emit fluorescent lights and their concentration in the pulp suspension is measured.

The principle of the measurement is to record the fluorescence intensity coming out of the flow cell 22 at a certain frequency and for a certain period of time. Time to time, a fluorescent contaminant passes in the flow cell 22 and is excited by the excitation beam 26. This leads to the fluorescence of the contaminant, which is detected by a detection system 28.

As mentioned above, most fluorescent dyes interact with the hydrophobic contaminants since the fluorescent probes are generally lipophilic. Therefore, several fluorescent dyes can be added to the pulp sample to measure the contaminants.

Figure 2:
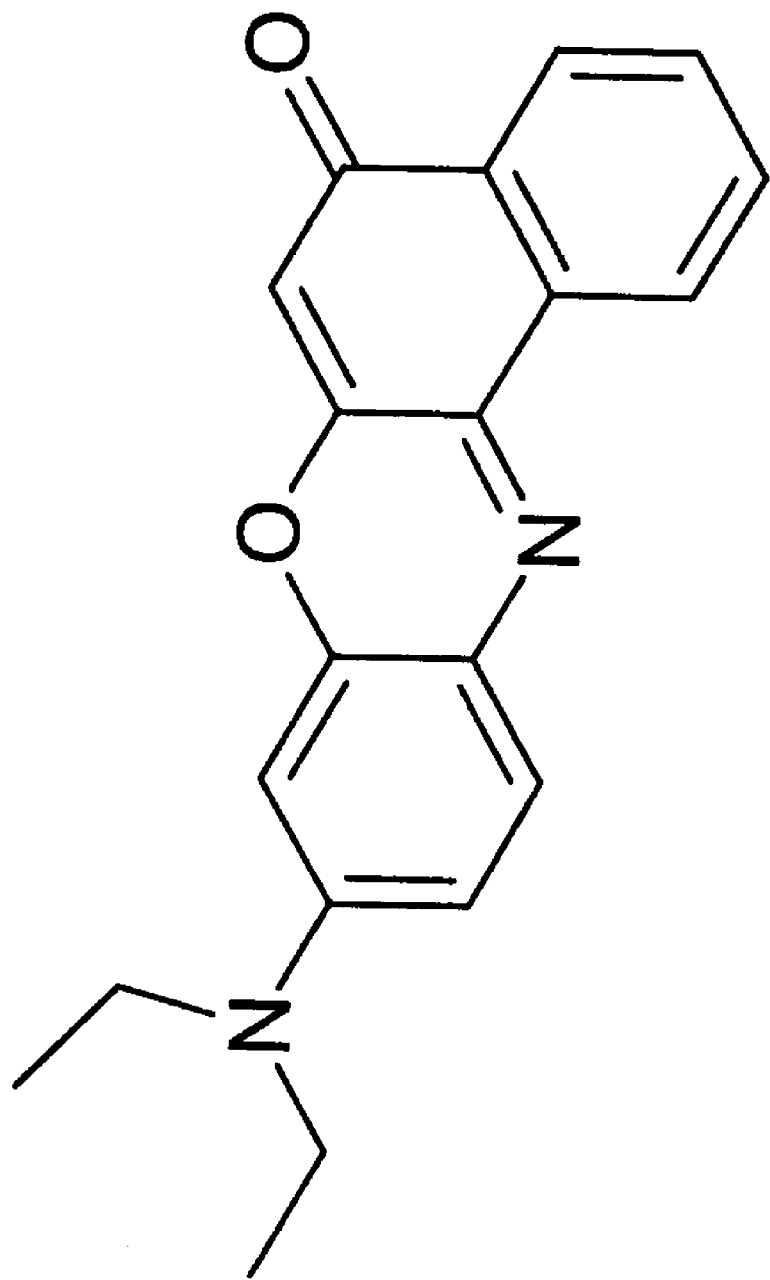
FIG. 2 is a schematic representation of the molecular structure of Nile red.

For example, Nile red, 9-diethylamino-5H-benzo[alpha] phenoxazine-5-one, shown in FIG. 2, is an environment sensitive fluorescent probe. The probe is weakly fluorescent in polar solvents (hydrophilic environment) and highly fluorescent in non-polar solvents (hydrophobic environment). This effect is illustrated in FIG. 3a, showing the low fluorescence of the probe in water and the high fluorescence of the probe in dichloromethane (hydrophobic solvent). In addition, there is shown in FIG. 3b that in presence of fibers, no fluorescence of the probe is induced. This shows that hydrophobic material can be detected in presence of fibers. Therefore, no separation of the contaminant-free particles from the particles including contaminants is required.

Nile red is a well-known probe in the biomolecular field and is largely used as cell membrane probe, lipid droplet detection, protein-lipid interaction monitoring, etc. Other examples, without being limitative, of fluorescent dyes which can be used are TNS (6-(p-toluidino)-2-naphthalenesulfonate sodium salt), ANS (8-anilino-1-naphthalenesulfonate ammonium salt), Prodan (6-Propionyl-2-dimethylaminonaphthalene), Patman (6-hexadecanoyl-2-(((2-(trimethylammonium)ethyl)methyl)amino)-naphthalene chloride), Laurdan (6-Dodecanoyl-2-dimethylaminonaphthalene), Dapoxyl™ (5-(4"-dimethylaminophenyl)-2-(4'-sulfonylphenyl)oxazole, Acrylodan (6-acryloyl-2-dimethylaminonaphthalene), etc.

Dye molecules interacting with other constituents of the pulp suspension, mostly fibers, do not show fluorescence as shown in FIGS. 3 and 4. In FIG. 4, there are shown recycled pulp constituents, collected on a filter and dyed with a fluorescent dye such as Nile red. In FIG. 4a, there is shown some stickies (appearing red due to the dye), some coating particles not dyed by the fluorescent dye (blue), some brown fibers and white fibers (appearing reddish due to the dye). Under visible light, all the constituents of the pulp suspension are visible making it difficult to identify the stickies part. Upon UV excitation, only the fluorescent particles are visible. In FIG. 4b, there is shown the blue fluorescence from white fibers (containing optical brighteners) and red fluorescent contaminants (dyed with the fluorescent probe). In FIG. 4c, there is shown that only the red fluorescent contaminants are visible when using a proper filter to cut the blue fluorescence.

As mentioned above, the principle of the measurement is to record the fluorescence intensity coming out of the flow cell at a certain frequency and for a certain period of time. The excitation time scale is approximately $10^{-15}$ s and the fluorescence lifetime scale is approximately $10^{-9}$ S. These are typical time scales, but the method is not limited to these. These fast times allow the fluorescence measurement of particles in high flow rate.

Figure 5:
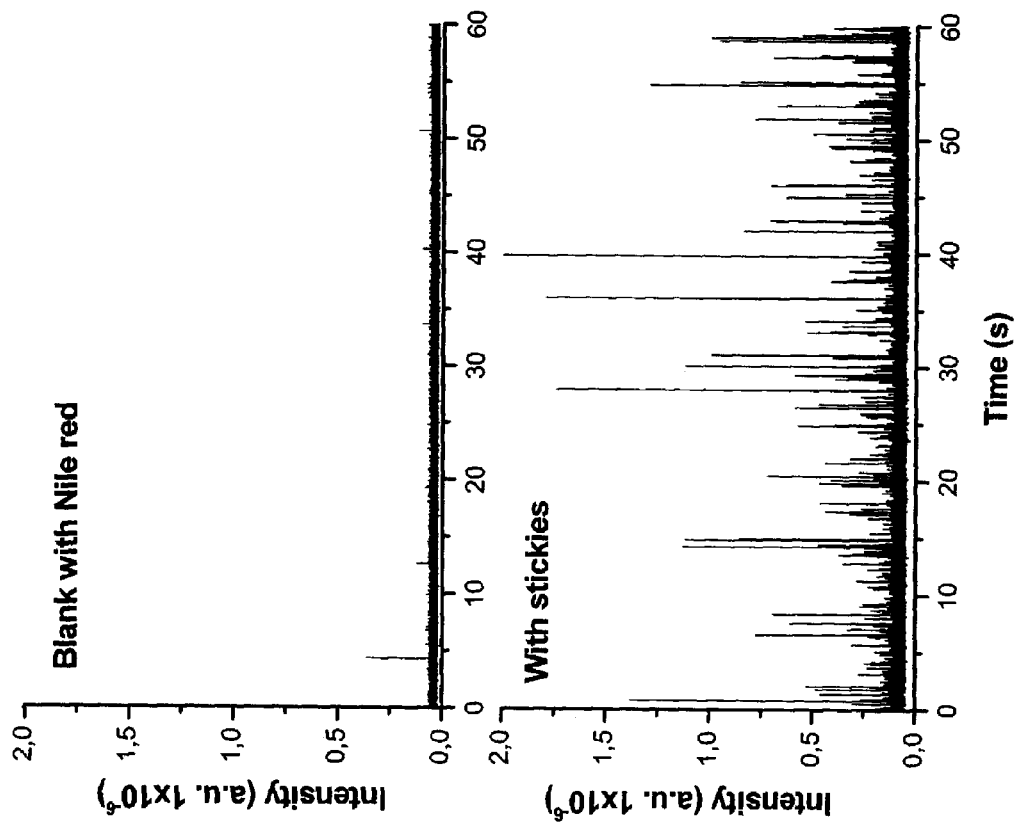
FIG. 5a is a graph showing the fluorescence of a virgin (contaminant free) pulp suspension with Nile red.
FIG. 5b is a graph showing the fluorescence of the same suspension with stickies added (acrylic based pressure sensitive adhesive)

As shown in FIG. 5, by recording the fluorescence intensity against the time, peaks of fluorescence are observed. Because the probability of a contaminant to pass by the flow cell is directly dependent of the concentration of contaminants in the suspension, the number of peaks for a certain period of time is proportional to the concentration of contaminants. Many parameters can affect the sensibility of the measurement: the intensity of the excitation light, the slit openings of the excitation and emission, and the sensibility of the detector. This is not intended to constitute an exhaustive list.

The sensibility of the measurement also depends on the size (diameter) of the flow cell and the flow rate. Bigger is the flow cell, lesser the excitation beam penetration is important, especially for a sample having a very high diffusion coefficient as a pulp suspension. Also, higher is the flow rate, lesser time is available for the detector system to perform the measurement.

The sensibility of the measurement also depends on the pulp consistency. Higher is the consistency, more diffusion is present and lesser light is available for the excitation. Also, at higher consistency, fibers can mask some contaminants.

The frequency of the recording also affects the sensibility of the measurement. A recording at high frequency ensures the detection of more contaminants, but leads to a larger data set to store and analyze. It is also possible that at high frequency, the same contaminant would give more than one peak and be interpreted as more than one contaminant.

Still referring to FIG. 5, there is shown that to ensure that no fluorescence was induced by the fibers suspension under the experimental set-up, a clean fiber suspension was made using virgin bleached Kraft fibers (laboratory blotters) (FIG. 5 a). To this pulp suspension was added a contaminated pulp made of the same blotters coated with a pressure sensitive adhesive (acrylic based) (FIG. 5b). The results confirm that no fluorescence is observed without the presence of contaminants. It shows also that contaminants can be easily detected using the method described above.

Figure 6:
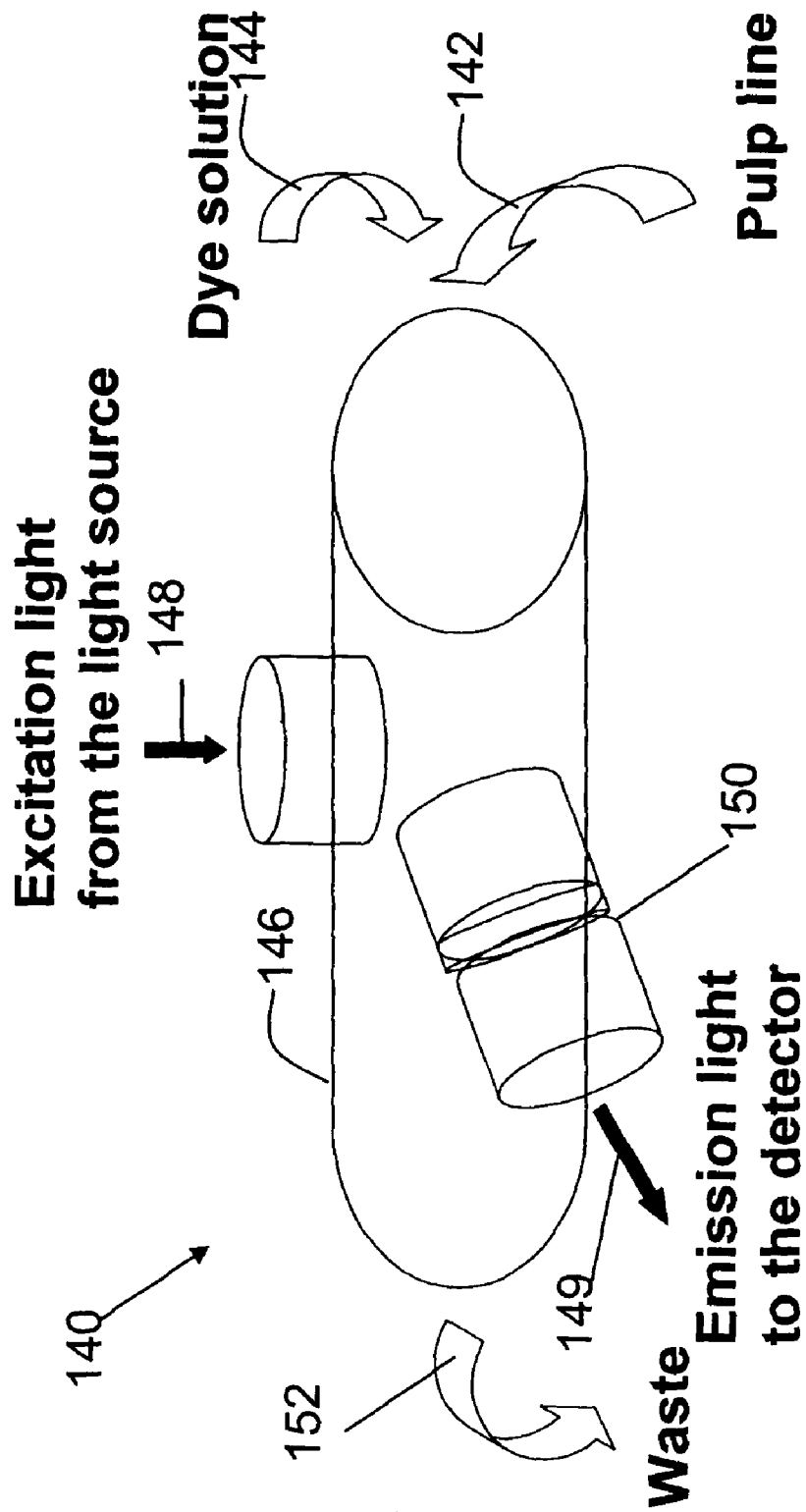
FIG. 6 is a schematic simplified set-up for an automatic contaminant sensor.

Referring to FIG. 6, it will be seen an equipment 140 intended to perform the measurement in a continuous way in the mill. First the equipment includes a pulp stream inlet 142 for introducing pulp, which can be already diluted at the right consistency and a dye inlet 144 for introducing a fluorescent dye to the pulp. The fluorescent dye can be already in solution. In an embodiment, the fluorescent dye is added in the pulp flow far enough from the detecting part to ensure a proper mixing of the fluorescent dye with the furnish. The flow cell 146 can be a simple glass tube. Both the excitation and emission lights 148, 149 can be brought to the flow cell 146 by optical fibers (not shown). A proper filter 150 can be used in the emission path to ensure no excitation light is detected by the detector (not shown). A person skilled in the art will appreciate that the optical filter 150 can be replaced by a monochromator. The equipment 140 also includes a waste outlet 152 allowing the pulp and dye mixture to exit from the flow cell 146.

Three major kinds of excitation lights are available: LED, lamp (halogen, xenon, tungsten, etc.), and solid-state laser. A green LED provides a quasi-monochromatic excitation light at 518 nm. This device is a relatively inexpensive device, but provides the lower power light (about 35 μW). The solid-state laser provides the highest monochromatic intensity light (25 mW, at 532 nm), but is the more expensive device. A halogen lamp provides a compromise between the high price of the solid-state laser and the low power LED. In this case, optical filters or a monochromator should be used to select the desired excitation wavelength.

The excitation light is selected as a function of its wavelength and in accordance with fluorescent dye added to the paper pulp suspension.

EXAMPLES

Figure 7:
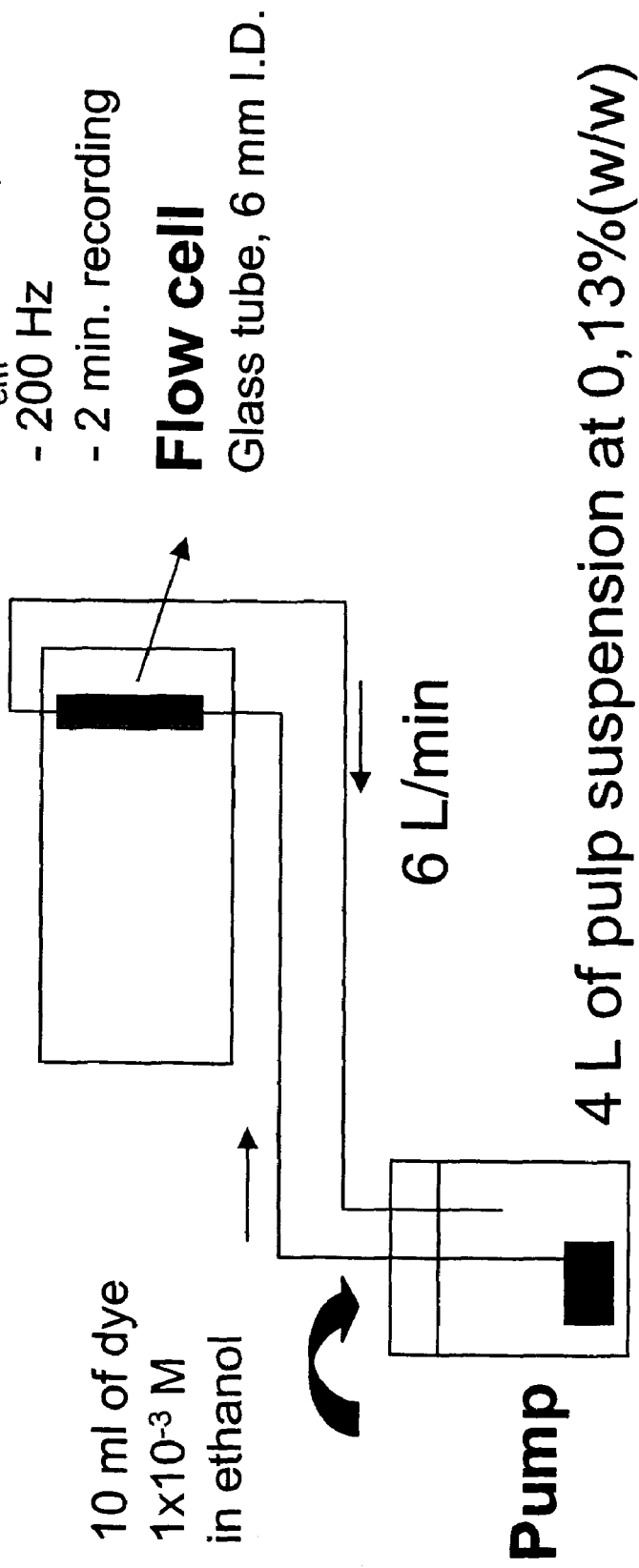
FIG. 7 is a schematic illustration of an experimental set-up.

Referring to FIG. 7, it will be seen an experimental set-up for measuring the contaminants in a paper pulp sample. Fluorescence measurements were obtained using a double monochromator Fluorolog 2 instrument. The excitation wavelength, provided by a 250 W tungsten lamp, was fixed at 550 nm and the emission wavelength was fixed at 650 nm. The excitation and emission slits were opened at 2 and 3 mm, respectively. The fluorescence was recorded at 90° of the excitation beam from a flow cell. The flow cell was a simple 8 cm long glass tube with an inside diameter of 6 mm. A flow of 6 L/min was obtained for a pulp consistency of 0.13% (w/w) using a centrifugal pump. Except if mentioned otherwise, these parameters were kept constant for all the measurements and the measurements were recorded at 200 Hz.

Contaminants measurements obtained by fluorescence were compared to the results obtained with the conventional laboratory method for stickies measurement (using a Pulmac for screening and Clemex images analysis).

The fluorescent dye used, Nile red, was purchased from TCI America. The dye was dissolved in ethanol at $1\times10^{-3}$ M before being added to the pulp suspension.

In all cases, samples from the feed, accept, and reject of a primary fine screening stage were used for the measurements. The primary fine screening was chosen in order to have the same pulp sample with different stickies concentrations. For the measurements, the pulp sample was diluted, usually to 0.13% (w/w), with hot tap water (40-45° C.) to a final volume of 4 L. A predetermined volume of the dye solution was added to the pulp suspension and the mixture was stirred for few minutes with a mechanical stirrer. The pump was then started and allowed to run for about 1 minute before starting the measurement. During the measurement, no stirring was applied and the pulp was kept suspended by the return of the flow in the bucket.

Samples from a Deinked Pulp Processed a First Paper Pulp Plant

Figure 8:
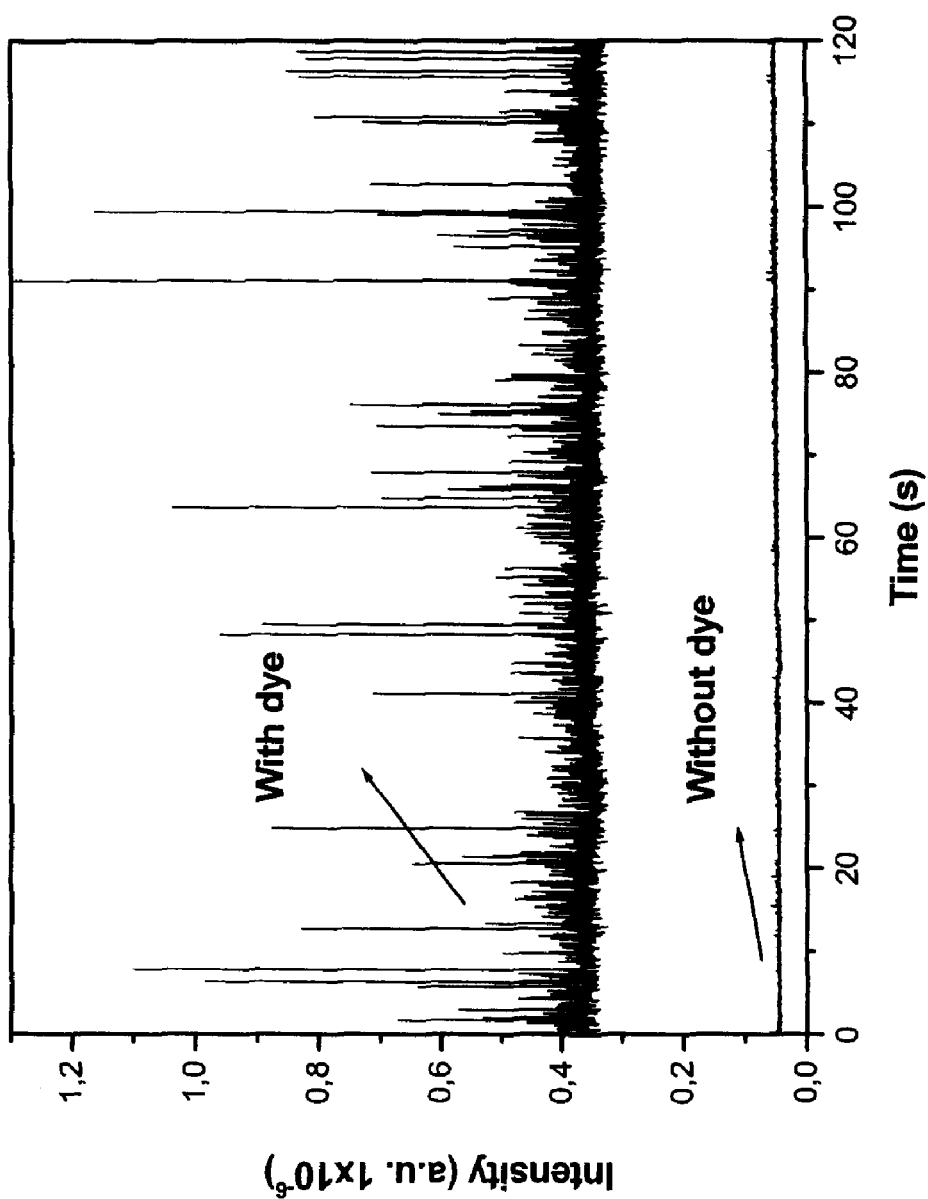
FIG. 8 is a graph showing the fluorescence profiles of a deinked pulp sample from the reject of a primary fine screening of a first paper pulp plant.

Referring to FIG. 8, there is shown that the fluorescence profile of a pulp suspension sampled at the mill without dye shows no fluorescence peak other than the background noise. This shows that under the experimental conditions, no intrinsic fluorescence from the pulp constituents is detected. Still referring to FIG. 8, there is shown the fluorescence intensity profile of the same pulp suspension with the dye added. The presence of the dye induces two important changes: 1—the presence of fluorescence peaks attributed to the hydrophobic contaminants, 2—the shift of the base line to a higher value of fluorescence. This shift can be due to the presence of hydrophobic colloids and/or secondary stickies. Because these particles are very small (<25 μm), they would be detected continually leading to a steady intensity.

Figure 9:
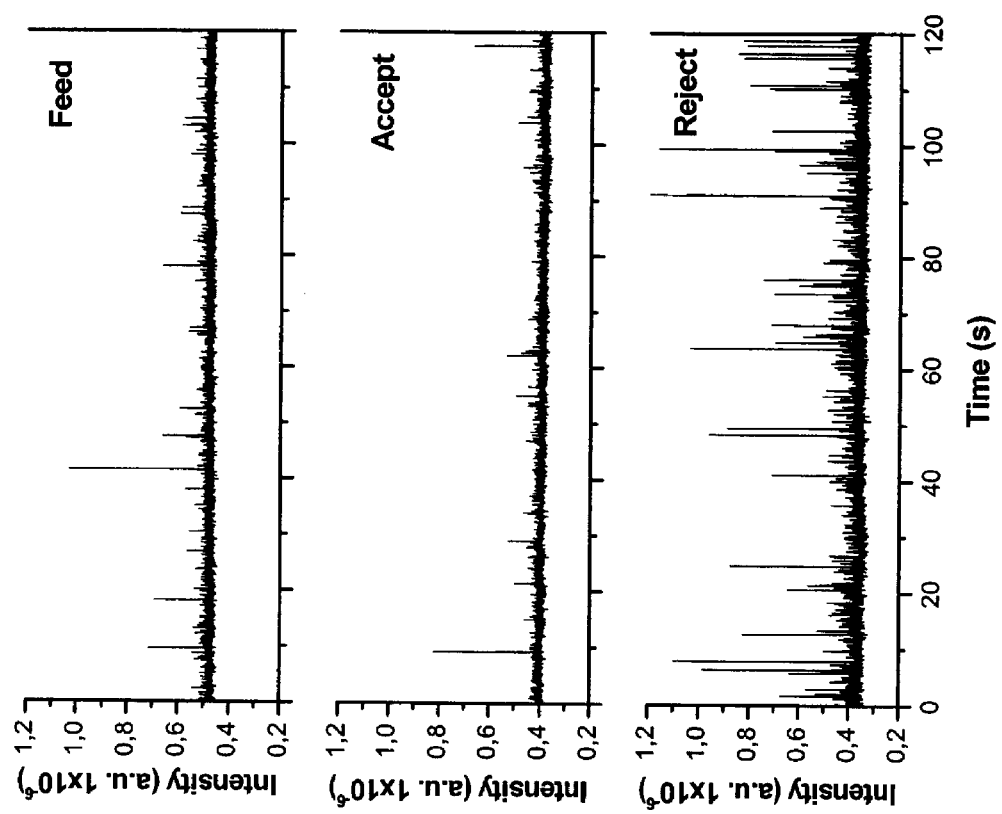
FIG. 9 is a graph showing the fluorescence profiles of deinked pulps sampled at a primary fine screening of the first paper pulp plant.

Referring to FIG. 9, there is shown the fluorescence profiles of pulps sampled at the feed, accept and reject of a primary fine screening (deinked pulp, first paper pulp plant). Visually, it can be seen that the number of peaks decreases from the reject, to the feed and to accept following the logic of the screening effect on contaminants. The screening step consists of passing the pulp suspension trough a basket having well defined slot size. Small pulp components pass trough the basket and go to the accept. Larger particles are retained by the basket and go to the reject. Following this process, the accept contains less and smaller contaminants, in comparison with the feed. On the other side, the reject contains more and larger contaminants, in comparison with the feed and the accept.

Figure 10:
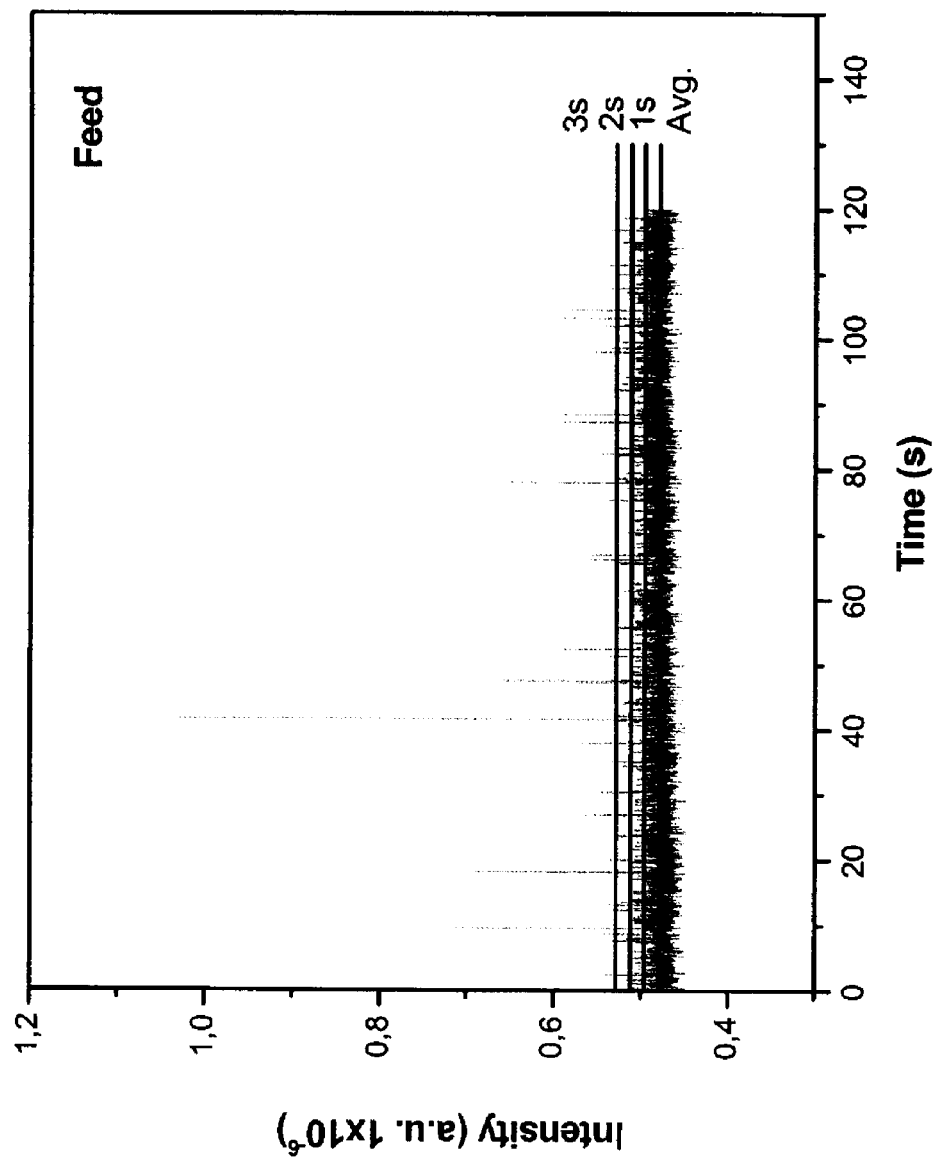
FIG. 10 is a graph showing the fluorescence profiles of a deinked pulp sample from the feed of the primary fine screening of the first paper pulp plant, the lower intensity at which the peaks start to be considered is manually fixed at average 2 s.
Figure 11:
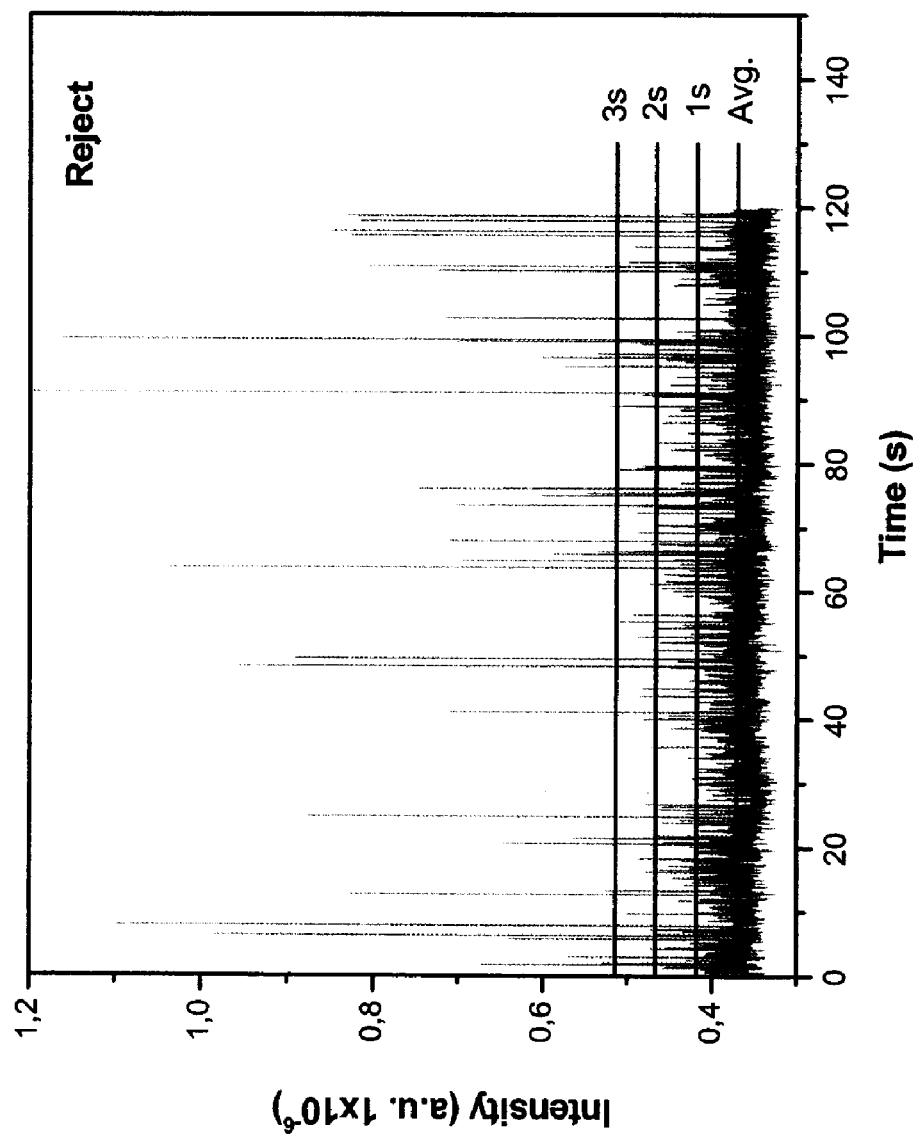
FIG. 11 is a graph showing the fluorescence profiles of a deinked pulp sample from the reject of the primary fine screening of the first paper pulp plant, the lower limit determination for a sample with a high contaminants level is set at average is.

The data analysis was performed in a semi-automatic way. The average intensity was plotted on the fluorescence profile along with the average plus 1 to 3 times the standard deviation (s) as shown in FIG. 10. One of these three lines ($1s$, $2s$, $3s$) was chosen as the minimum limit at which the intensity is no more considered as the noise. This limit can differ from sample to sample depending on the concentration of contaminants as shown in FIG. 11.

Two different ways of data analyzing were performed. One is using the sum of all the peaks intensities, over the lower limit established (total intensity) and the other one is using the number of peaks. Logically the first approach seems more appropriate because it will neglect the small noise peaks that could be considered. On the other hand, it will tend to give more weight to large contaminants. The second approach will greatly depend on the lower limit fixed because any small noise peaks over this limit will be considered as one contaminant.

Figure 12:
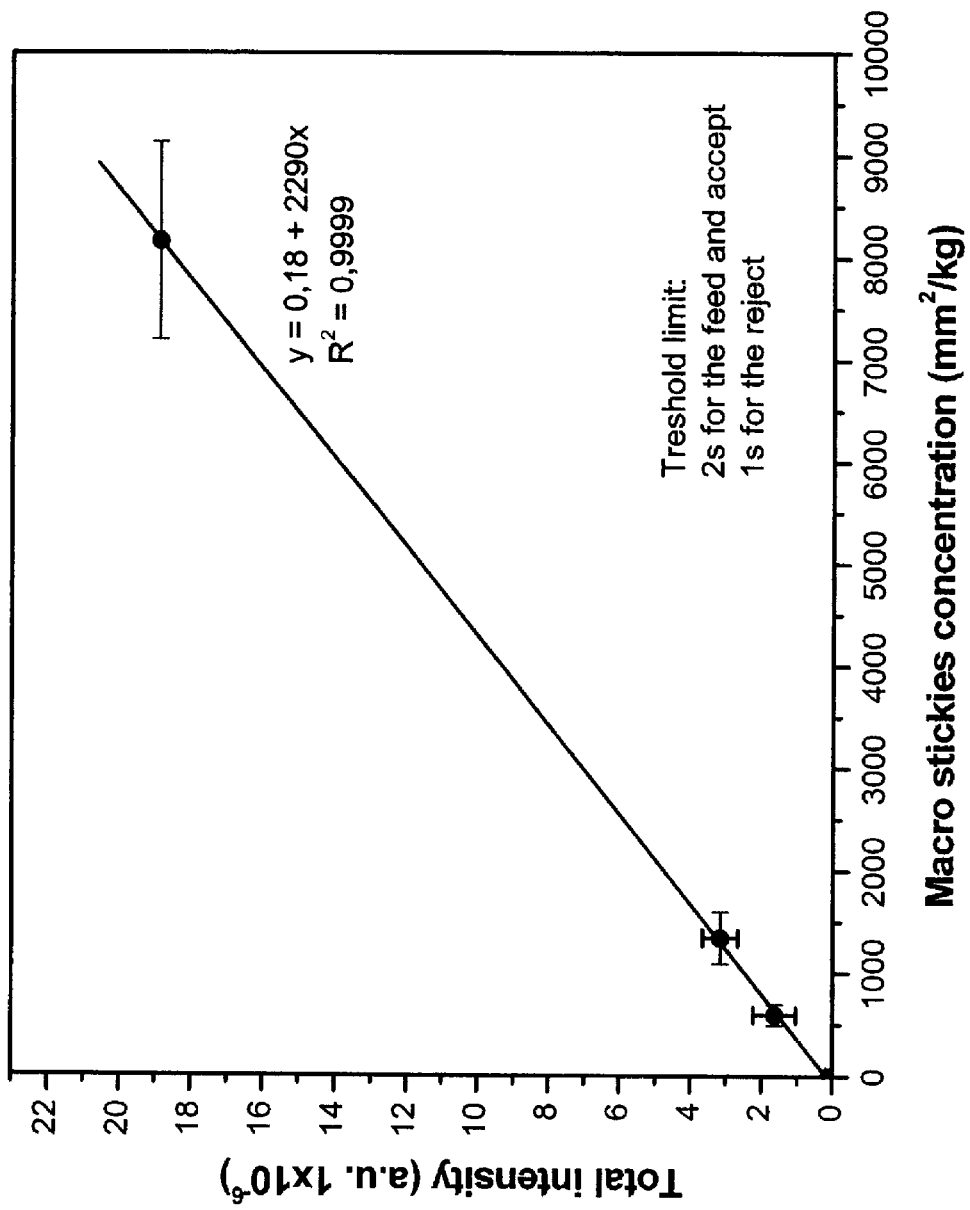
FIG. 12 is a graph showing the correlation between the fluorescence total intensity and the macro stickies concentration as measured at the laboratory with samples from the primary fine screening of the deinked pulp at the first paper pulp plant (200 Hz; 0.13% consistency; $2.5 \times 10^{-6}$ M Nile Red)
Figure 13:
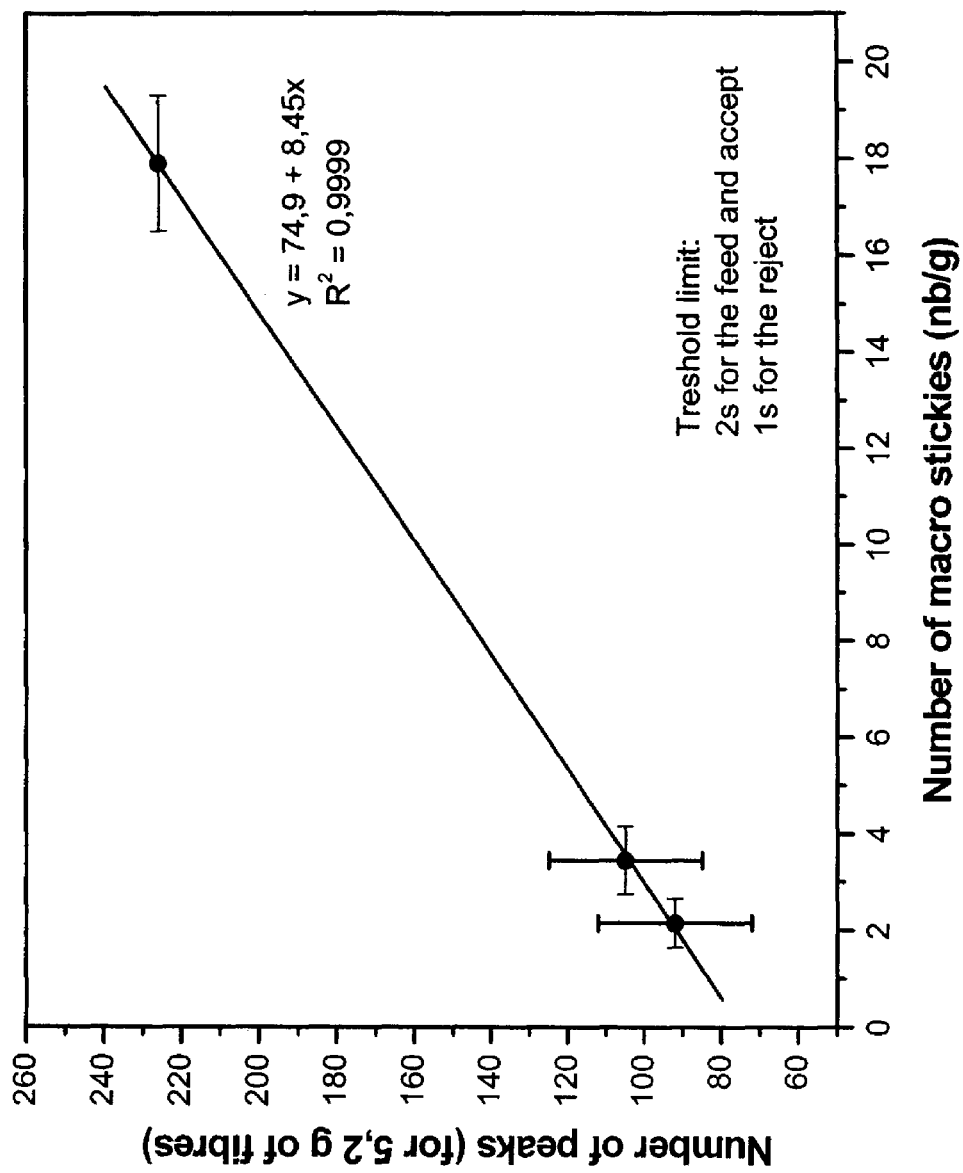
FIG. 13 is a graph showing the correlation between the number of peaks and the number of macro stickies as measured at the laboratory with samples from the primary fine screening of the deinked pulp at the first paper pulp plant (200 Hz; 0.13% consistency; $2.5 \times 10^{-6}$ M Nile Red)

The results of the data analyzed for the primary fine screening of the deinked pulp of the first paper pulp plant are shown in FIGS. 12 and 13. Using the total intensity, a good correlation between the fluorescence measurements and the stickies concentration measured with the conventional laboratory methods is obtained (FIG. 12). The feed and accept samples were taken in duplicate, and in both cases the repeatability was good. A correlation between the number of stickies and the number of peaks can also be observed (FIG. 13). The number of stickies is rarely used for analysis and large errors are associated to the number of stickies and the number of peaks. For this reason, the use of the total intensity is preferred and was used for all the other analyses done.

Figure 14:
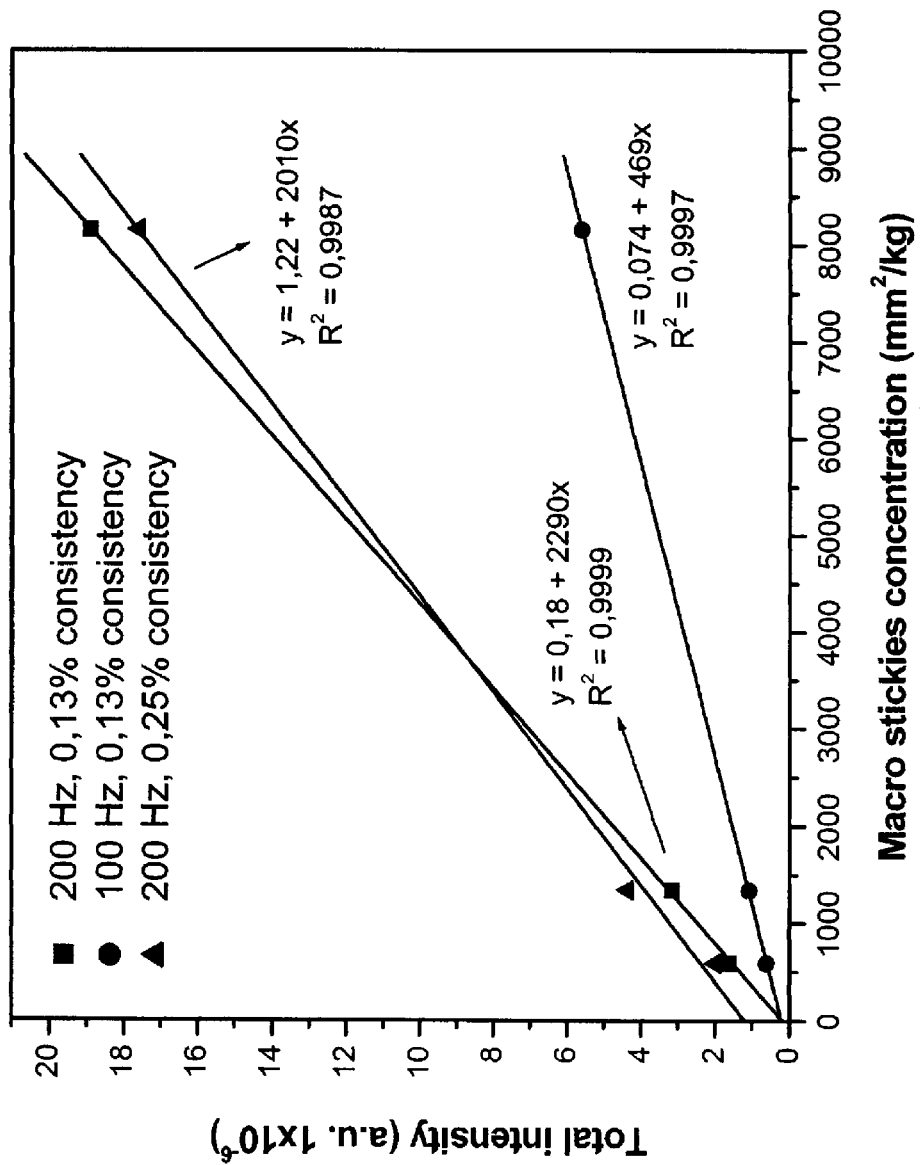
FIG. 14 is a graph showing the impact of the recording frequency and pulp consistency on the fluorescence response with samples from the primary fine screening of the deinked pulp at the first paper pulp plant ($2.5 \times 10^{-6}$ M Nile Red)

Referring now to FIG. 14, it will be seen the impacts of the recording frequency and of the pulp consistency. From recording at 200 Hz (one measurement each 5 ms) to 100 Hz (one measurement each 10 ms), a good correlation between fluorescence intensity and the stickies concentration is kept, but an important decrease in the sensibility (slope of the line) of the measurement is observed. Going from 0.13% to 0.25% consistency did not change the linear relation and the sensibility of the measurement. No higher consistencies have been checked due to the limit of the pump used.

As described previously, many other parameters affect the sensibility of the measurements. For example, the decrease of the sensibility at 100 Hz can be overcome by decreasing the flow rate in the flow cell.

Samples from a Deinked Pulp from a Second Paper Pulp Plant

Figure 15:
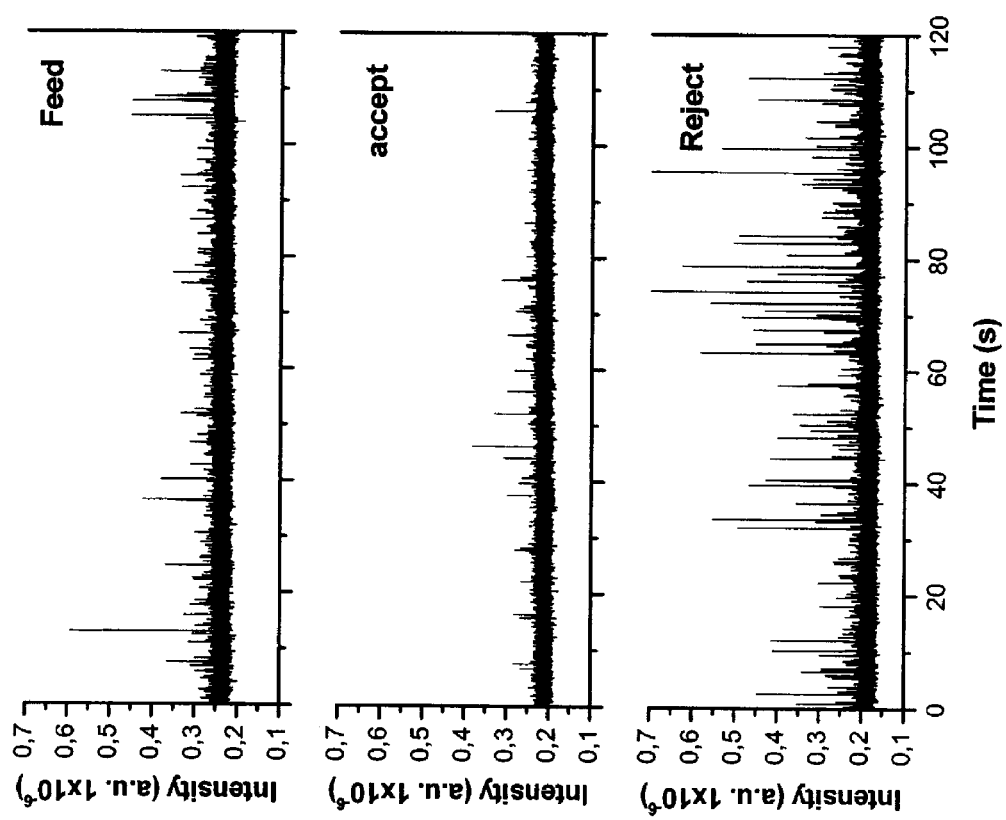
FIG. 15 is a graph showing the fluorescence profiles of pulps sampled around the primary fine screening at a second paper pulp plant.
Figure 16:
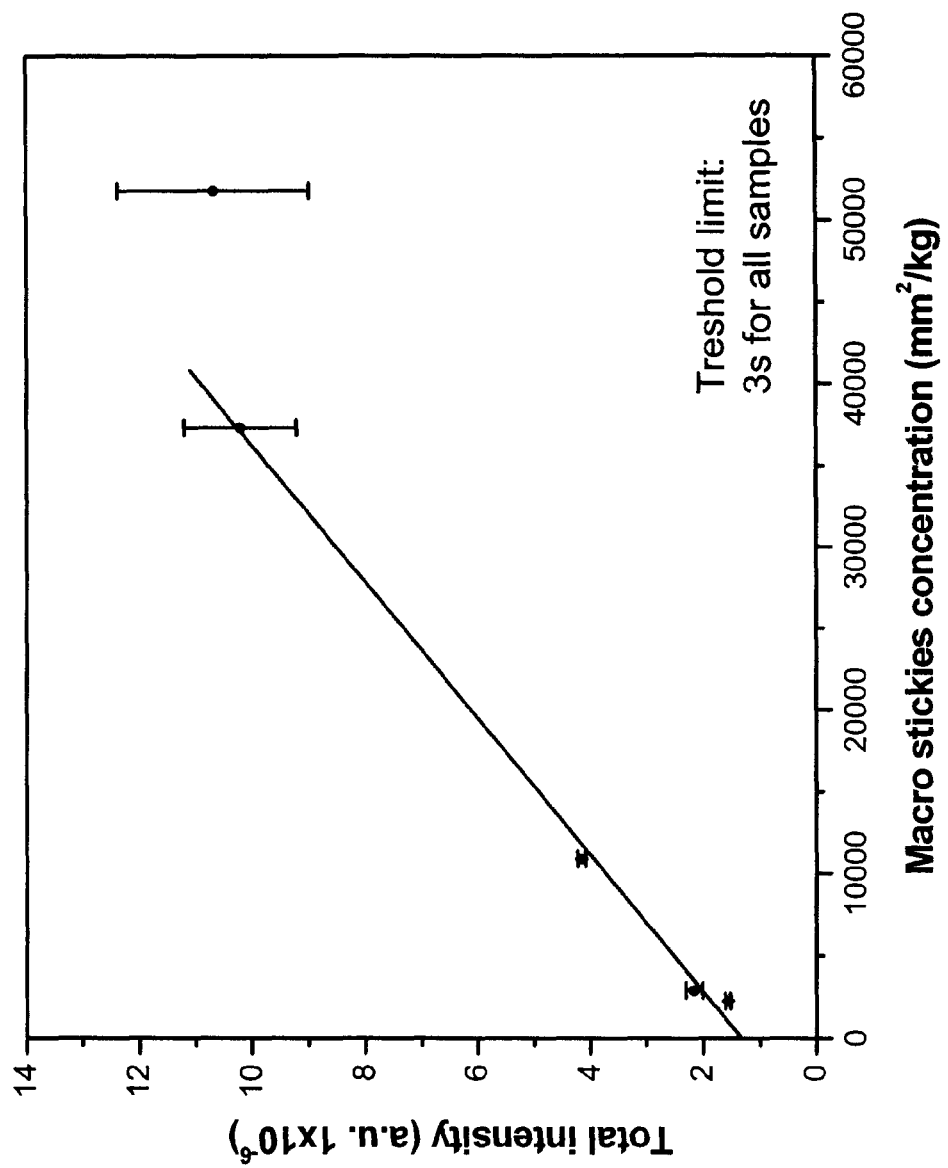
FIG. 16 is a graph showing the correlation between the fluorescence measurement and the macro stickies concentration as measured at the laboratory with samples from the primary fine screens at the second paper pulp plant (200 Hz; 0.13% consistency; $2.5 \times 10^{-6}$ M Nile Red)

Referring now to FIGS. 15 and 16, it will be seen that pulp samples from the feed, accept and reject of the primary fine screening stage of the deinked pulp line at a second paper pulp plant were also analyzed. These samples were measured under different conditions than the first paper pulp plant ones, so no direct comparison can be done between them. The second paper pulp plant is operating two primary fine screens in parallel, having the same feed but different baskets. In comparison with the first paper pulp plant samples, the stickies concentrations measured in the second plant pulp suspensions are much higher, giving another scale of comparison.

Referring to FIG. 16, there is shown that a quasi-linear relation is observed between the fluorescence measurements (total intensity) and the results obtained with conventional laboratory methods. The repeatability for the first 3 points, two accepts and one feed, is very good. The precision of the fluorescence method is also highlighted by the first two points (the two accepts) where a slight difference in the stickies concentration measured with the conventional laboratory method is reproduced by the fluorescence method.

Samples from OCC from a Third Paper Pulp Plant

Results showed previously were taken from white fiber grades (first and second paper plant). A similar study was performed with a brown fiber grade. Samples from the primary fine screening stage at a third paper pulp plant during the production of a brown liner were studied.

Figure 17:
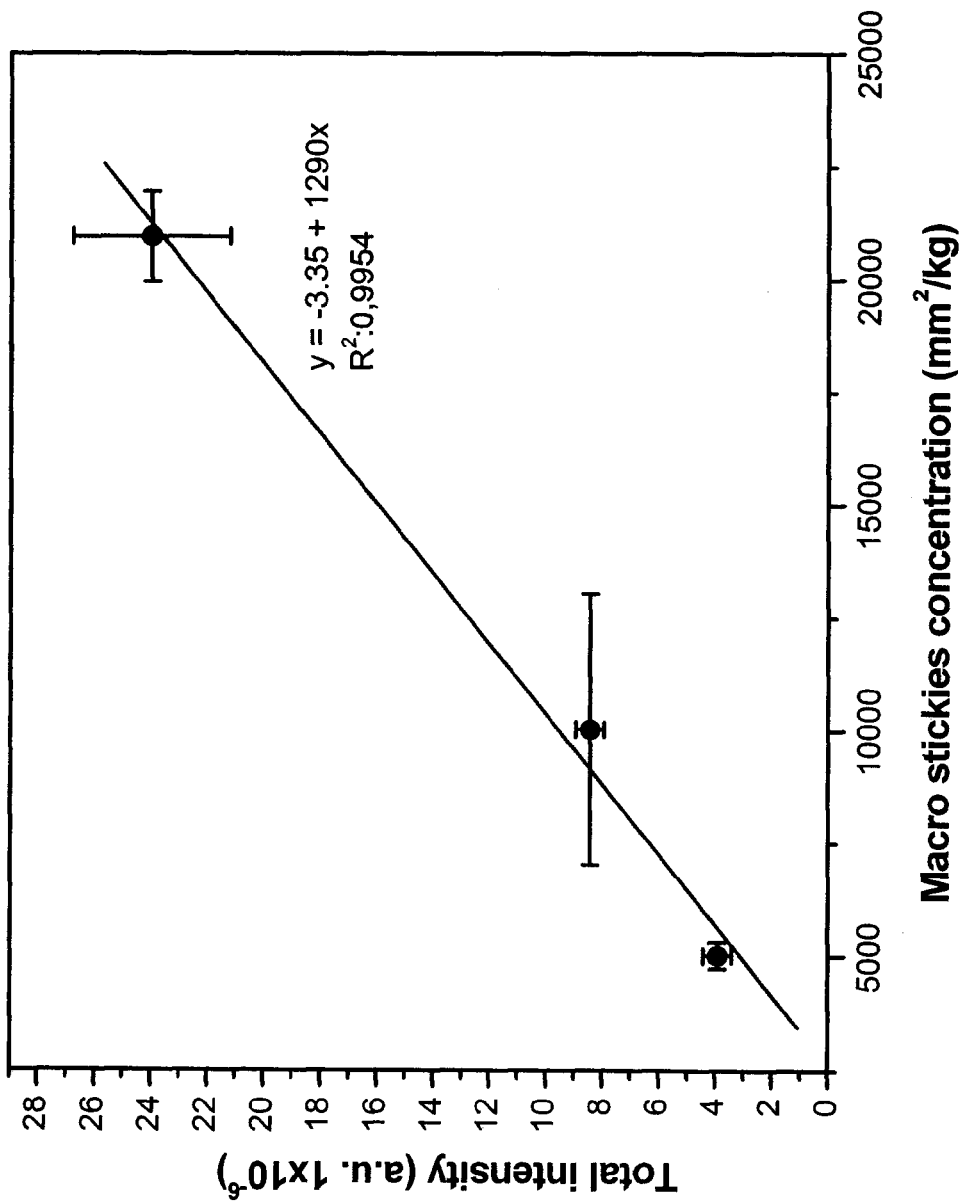
FIG. 17 is a graph showing the correlation between the fluorescence method and the macro stickies concentration for a brown fiber grade (OCC: Old Corrugated container; Brown packaging paper) with samples from a primary fine screen of a third paper pulp plant (200 Hz; 0.13% consistency; $5 \times 10^{-6}$ M Nile Red)

Referring to FIG. 17, it will be seen the correlation between the fluorescence results and the stickies measurement with conventional laboratory methods. A good correlation was obtained showing that the method can be applied to almost any pulp sample.

FIG. 17 shows also the error bars associated with the duplicate measurements for both the fluorescence method and the conventional laboratory image analysis method. The fluorescence method shows a very good repeatability (difference between the duplicate of 6% for the feed and 12% for the accept and reject). The repeatability is also good for two samples using the conventional laboratory image analysis method, 6% difference for the accept and reject, but low for the feed, 30% difference. The stickies counting method by image analysis requires more manipulations increasing the probability of experimental errors. Also, at high stickies concentrations, less pulp can be used for the measurement, decreasing the precision of the method. The advantage of the fluorescence method is that there is no limit on the amount of pulp to be used for the test and the recording time can be increased as much as needed to get the reproducibility needed.

Figure 18:
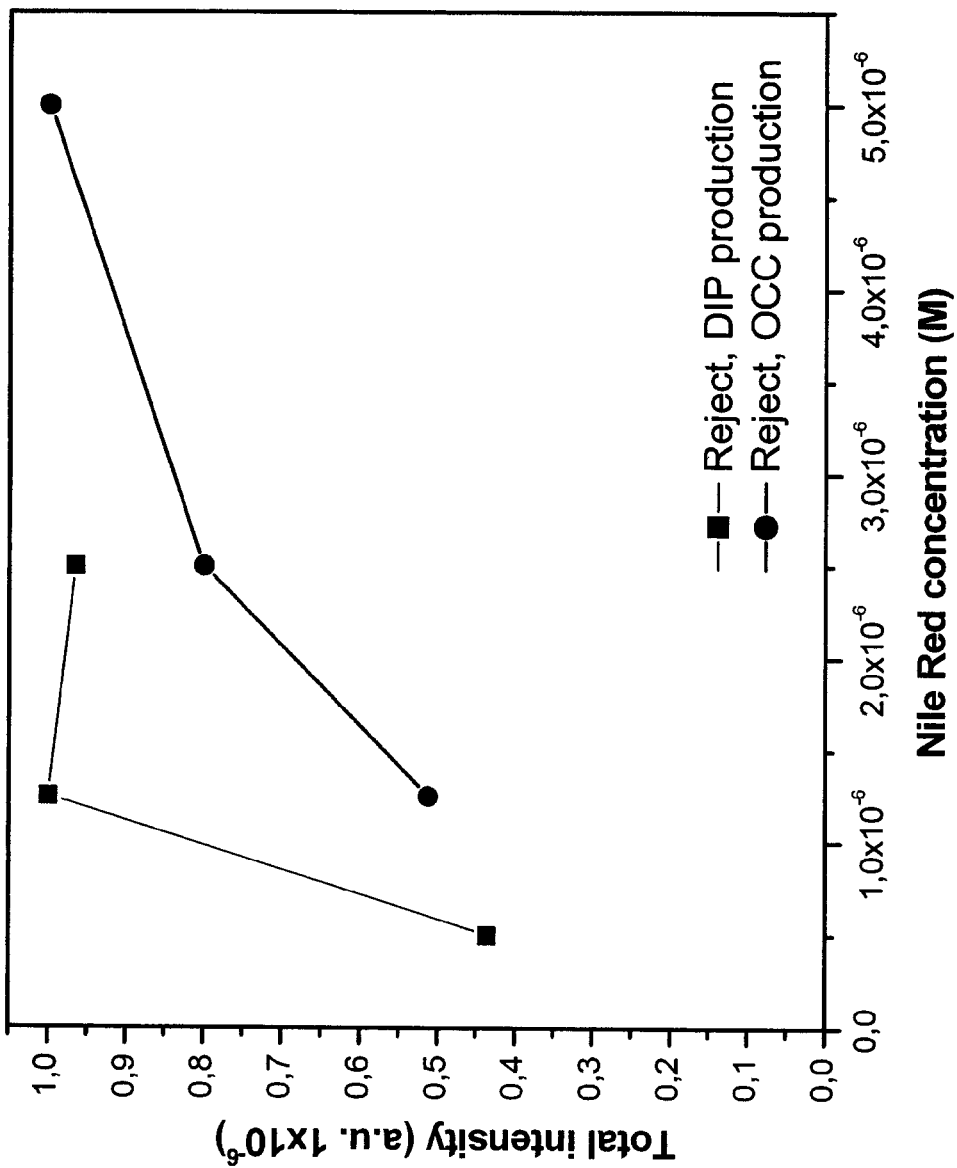
FIG. 18 is a graph showing the effect of the dye concentration on the fluorescence response of white (DIP: Deinked pulp line) and brown (OCC) pulps.

One important difference observed between the white grades and the brown grade is the amount of dye needed to make the measurement. Referring to FIG. 18, there is shown the fluorescence response of two fine screening rejects pulp as a function of the dye concentration. It can be observed that for the white grade (second pulp paper plant), a plateau is obtained with a dye concentration of $1.2 \times 10^{-6}$ M. For the brown grade (third pulp paper plant), more dye was needed to reach this plateau, which was just beginning to show at $5 \times 10^{-6}$ M.

With the method and the apparatus described above, the contaminants can be measured directly in a pulp suspension. The method shows a good precision and a good correlation with the conventional laboratory method of stickies measurement by screening and image analysis. It is fast (few minutes) and easy to perform. The method can be easily used as an online automatic sensor on a pulp preparation process. The method can either be performed manually or online in an automatic way, in a pulp preparation process.

The apparatus could be provided in the form of a portable commercial instrument. This kind of instrument can be used in laboratories and in the mills.

Tests were conducted at a paper mill with a portable instrument to 1) validate the reliability thereof and to 2) evaluate the impact of the mixing time, after the addition of the fluorescent dye, on the results. For all measurements, we used 4 litres of pulp at a 0.13% consistency. All dilutions were done with tap water. The pulp was pumped in loop at a flow rate of 4.2 L/min with a submersible pump. The data were recorded at a frequency of 200 Hz for 120 seconds. The dye concentration was $2.5 \times 10^{-6}$ M. A threshold of 3 times the standard deviation (1) of the background was used to analyse all the data (i.e. peaks showing a higher intensity than 3 times the standard deviations of the background level were considered as peaks resulting from contaminants.).

The results obtained show that the fluorescent dye and the pulp suspension must be mixed together for a sufficient period of time in order to obtain constant results. According to the conditions prevailing at the mill where the experiments were conducted, a mixing period of 15 to 20 minutes was required for the mixture to stabilize and reach constant results. During the first minutes after the addition of the dye, we observed a reduction of the average intensity (background) and an increase in the number and intensity of the peaks. This mixing time could correspond to the time required by the stickies (i.e. contaminants) to absorb the dye. However, various parameters might influence the required mixing time such as shear, temperature, dye concentration and pulp consistency.

A photomultiplier tube (PMT) based instrument could also be used to perform the tests.

Depending on the contaminant nature, the fluorescent probe and the measuring conditions can be adapted.

The method can be applied and the apparatus can be used either on virgin pulp suspensions or recycled pulp suspensions, i.e. recovery fibers.

Using the method and the apparatus, the mill can perform online detection, quality control of raw material, process control, automatic control of additive dosages used for stickies control, live results of trials, data bank of contaminant level versus process conditions, etc. All this information can ultimately lead to a better control of contaminants by the mill and help to maintain low contamination in the end product.

As mentioned herein above, the total fluorescence intensity can be used to determine by correlation the concentration of contaminants in the pulp suspension. But the fluorescence profile gives also other useful information such as the number of peaks and the intensity of these peaks. A correlation between the number of peaks and the number of contaminants can also be established. This correlation between the peaks' number and the contaminants' number in addition to a correlation between the average peaks' intensity and the average contaminants' specific surface are shown in Table 1.

TABLE 1

Correlation between the number and the specific size of the contaminants and the number of peaks and the average peak intensity from the new fluorescence method.

| | Contaminants concentration ($mm^2$/kg) Conventional method | Contaminants concentration (contaminant/g) CRD method | Number of peaks Fluo. method | Average specific surface ($mm^2$) Conventional method | Average peak intensity a.u. Fluo. method |
|---|---|---|---|---|---|
| PFS reject | 13874 | 30.0 | 181 | 0.77 | 5664 |
| Pulper outlet | 12596 | 13.3 | 58 | 1.13 | 10923 |

PFS: primary fine screen

In this case, two different samples, having similar contaminants concentration in term of $mm^2$/kg, were compared. Despite the fact that both samples showed similar contaminants concentration, the pulper outlet sample had less contaminants, but the contaminants were larger, in comparison with the contaminants found in the reject of the primary fine screen (PFS). This was also seen with the fluorescence method were the number of peaks was less for the pulper outlet sample but the average peak intensity was higher. This shows that the fluorescence method could provide, in addition to the contaminants concentration, the number of contaminants and their specific size. To a larger extent, it is possible that the fluorescence method could provide also the size distribution, via the peak intensities distribution of the contaminants in the sample.

The embodiments of the invention described above are intended to be exemplary only. The scope of the invention is therefore intended to be limited solely by the scope of the appended claims.

The invention claimed is:

1. A method for measuring the concentration of hydrophobic contaminants distributed in a paper pulp suspension, the method comprising:
   adding a lipophilic fluorescent dye to the paper pulp suspension including fibers and hydrophobic contaminants, the lipophilic fluorescent dye interacting with the hydrophobic contaminants exhibiting fluorescence, whereas the lipophilic fluorescent dye interacting with the fibers exhibiting substantially no fluorescence;
   submitting the paper pulp suspension including a mixture of fibers, hydrophobic contaminants, and lipophilic fluorescent dye to light characterized by a wavelength exciting the lipophilic fluorescent dye interacting with the hydrophobic contaminants to produce light emission signals;
   detecting the light emission signals by observing at least one of peaks of fluorescence against time and an average of fluorescent intensities; and
   evaluating the detected light emission signals to measure the hydrophobic contaminants by correlating the detected light emission signals to the concentration of contaminants.

2. A method as claimed in claim 1, comprising mixing the paper pulp suspension including the fibers, the hydrophobic contaminants, and the lipophilic fluorescent dye.

3. A method as claimed in claim 1, comprising sampling a paper pulp suspension flow to obtain the paper pulp suspension.

4. A method as claimed in claim 3, comprising diluting the sample to a predetermined consistency before submitting the sample to light.

5. A method as claimed in claim 1, comprising filtering the light emission signals.

6. A method as claimed in claim 1, comprising passing the paper pulp suspension including the fibers, hydrophobic contaminants, and lipophilic fluorescent dye through a selected one of a laser beam, a light emitting diode (LED) and a xenon lamp.

7. A method as claimed in claim 1, wherein the lipophilic fluorescent dye comprises 9-diethylamino-5H-benzo[alpha]phenoxazine-5-one.

8. A method as claimed in claim 1, wherein the lipophilic dye is an environmental sensitive dye showing high fluorescence in an hydrophobic environment.

9. A method as claimed in claim 1, comprising detecting the light emission signals with a selected one of an Avalanche photodiode, photodiode and a photomultiplier tube (PMT).

10. A method as claimed in claim 1, wherein the method is at least one of paper pulp suspension filtration free and paper pulp suspension screening free.

11. A method as claimed in claim 1, wherein the fluorescent dye has higher fluorescent intensities in hydrophobic environments than in hydrophilic environments and wherein the light emission signals comprise fluorescence intensities variations.

12. A method as claimed in claim 1, wherein said detecting comprises observing peaks of fluorescence against time and establishing that at least one of the number of peaks over a predetermined period of time and the total fluorescence intensity is proportional to the concentration of contaminants in the paper pulp suspension.

13. A method as claimed in claim 1, wherein said detecting comprises observing the average of the fluorescent intensities and establishing that the average of the fluorescent intensities is proportional to the concentration of contaminants in the paper pulp suspension.

14. The method defined in claim 1, comprising establishing a lower fluorescence intensity value and considering all the peaks which are greater than the lower fluorescence intensity value in the determination of the density of hydrophobic contaminants in the paper pulp suspension.

15. A method as claimed in claim 1, wherein said detecting comprises passing the mixture through an in-line mounted flow cell of a process line.

16. A method as claimed in claim 1, comprising removably mounting a portable monitoring device directly on a paper pulp process line before adding the fluorescent dye to the pulp suspension.

17. A method for monitoring hydrophobic contaminants in a paper pulp suspension containing hydrophilic fibers and hydrophobic contaminants, the method comprising:
   a) selecting a fluorescent dye having higher fluorescent intensities in hydrophobic environments than in hydrophilic environments,
   b) mixing the fluorescent dye with the paper pulp suspension to obtain a mixture containing fluorescent dye, hydrophilic fibers and hydrophobic contaminants, and
   c) monitoring the hydrophobic contaminants in the paper pulp suspension by observing at least one of peaks of fluorescence against time and an average of fluorescent intensities in a flow of the mixture obtained at step b) and analysing the fluorescence intensities variations in the mixture for correlating the monitored fluorescence intensities to the concentration of the hydrophobic contaminants.

18. The method defined in claim 17, wherein the peaks of fluorescence against time are observed and further comprising establishing that at least one of the number of peaks over a predetermined period of time and the total fluorescence intensity is proportional to the concentration of contaminants in the paper pulp suspension.

19. The method defined in claim 17, comprising diluting the paper pulp suspension to a predetermined consistency before step b).

20. The method defined in claim 17, wherein step c) comprises passing the mixture through an in-line mounted flow cell of a process line.

21. The method defined in claim 17, comprising the step of removably mounting a portable monitoring device directly on a paper pulp process line and conducting steps b) and c).

22. The method defined in claim 17, wherein step a) comprises selecting a lipophilic fluorescent dye.

23. The method defined in claim 17, wherein step c) comprises submitting the paper pulp suspension including the fibers, hydrophobic contaminants, and fluorescent dye to light characterized by a wavelength exciting the lipophilic fluorescent dye to produce light emission signals; and detecting the light emission signals and evaluating the signals to measure the hydrophobic contaminants.

24. The method defined in claim 17, comprising establishing a lower fluorescence intensity value and considering all the peaks which are greater than the lower fluorescence intensity value in the determination of the density of hydrophobic contaminants in the paper pulp suspension.

25. The method defined in claim 17, wherein the method is at least one of paper pulp suspension filtration free and paper pulp suspension screening free.

26. The method defined in claim 17, wherein the average of the fluorescent intensities is observed and further comprising establishing that the average of the fluorescent intensities is proportional to the concentration of contaminants in the paper pulp suspension.

* * * * *